US00PP24552P3

(12) United States Plant Patent
Leis et al.

(10) Patent No.: US PP24,552 P3
(45) Date of Patent: Jun. 17, 2014

(54) STRAWBERRY PLANT NAMED 'ISCHIA'

(50) Latin Name: *Fragaria L.*
Varietal Denomination: ISCHIA

(75) Inventors: Michelangelo Leis, Ferrara (IT); Alessio Martinelli, Ferrara (IT); Gianfranco Castagnoli, Quingentole (IT); Donata Azzolini, legal representative, Quingentole (IT); Pietro Castagnoli, legal representative, Quingentole (IT); Alessandro Castagnoli, legal representative, Quingentole (IT)

(73) Assignee: C.I.V.—Consorzio Italiano Vivaisti—Società Consortile A R.l., Comacchio FE (IT)

( * ) Notice: Subject to any disclaimer, the term of this patent is extended or adjusted under 35 U.S.C. 154(b) by 0 days.

(21) Appl. No.: 13/385,297

(22) Filed: Feb. 13, 2012

(65) Prior Publication Data

US 2012/0240297 P1 Sep. 20, 2012

(30) Foreign Application Priority Data

Feb. 14, 2011 (QZ) ..... PBR 20110358

(51) Int. Cl.
*A01H 5/00* (2006.01)

(52) U.S. Cl.
USPC ..... Plt./209

(58) Field of Classification Search
USPC ..... Plt./209, 208
See application file for complete search history.

*Primary Examiner* — Kent L Bell
(74) *Attorney, Agent, or Firm* — Foley & Lardner LLP

(57) ABSTRACT

A new and distinct variety of *Fragaria L.* named 'ISCHIA', characterized by the description herein.

4 Drawing Sheets

Latin name of the genus and species claimed: *Fragaria L.* Variety denomination: 'ISCHIA'.

PRIORITY CLAIM

This application claims the benefit of European Community Plant Variety Office Plant Breeders' Rights Application No. 2011/0358, filed Feb. 14, 2011.

BACKGROUND OF THE INVENTION

The present invention relates to a new and distinct strawberry variety named 'ISCHIA', which was the result of a controlled cross between the strawberry variety 'CIVRI30' (Breeder reference, unpatented) and a not released selection of Consorzio Italiano Vivaisti named 'O2N2-19'.

The progeny was first asexually propagated by stolons in S. Giuseppe di Comacchio Ferrara, Italy, in 2005.

The 'ISCHIA' variety was tested over the next several years in different European areas with continental climates. The tests started in 2006 and continued until 2010.

BRIEF SUMMARY OF THE INVENTION

Plants of the new Strawberry variety 'ISCHIA' can be distinguished from plants of the Strawberry variety 'CIVRI30' by the following unique combination of characteristics described in Table 1:

TABLE 1

| Comparison with Comparison Variety | | | |
|---|---|---|---|
| Denomination of similar variety | Characteristic in which the similar variety is different | State of expression of similar variety | State of expression of candidate variety |
| 'CIVRI30' | Plant Vigor | Weak to Medium | Strong |
| | Leaf Size | Small to Medium | Medium to Large |
| | Fruit Color | Orange Red | Medium Red |

Plants of the new Strawberry variety 'ISCHIA' can be distinguished from plants of the parent Strawberry variety 'O2N2-19' by the following unique combination of characteristics described in Table 2:

TABLE 2

| Comparison with Parent Variety: | | | |
|---|---|---|---|
| Denomination of similar variety | Characteristic in which the similar variety is different | State of expression of similar variety | State of expression of candidate variety |
| 'O2N2-19' | Fruit color | Deep red (RHS53A) | Medium red (RHS46B) |
| | Fruit shape | Obloid | Conical |

Asexual reproduction of this new variety by stolons shows that the foregoing and all other characteristics and distinctions come true to form and are established and transmitted through succeeding propagations. The new variety reproduces true to type.

BRIEF DESCRIPTION OF THE PHOTOGRAPHS

The accompanying photographs illustrate the overall appearance of the new Strawberry 'ISCHIA' showing the colors as true as is reasonably possible with colored reproductions of this type. Colors in the photographs may differ slightly from the color value cited in the detailed botanical description, which accurately describe the color of 'ISCHIA'.

Figure 1:
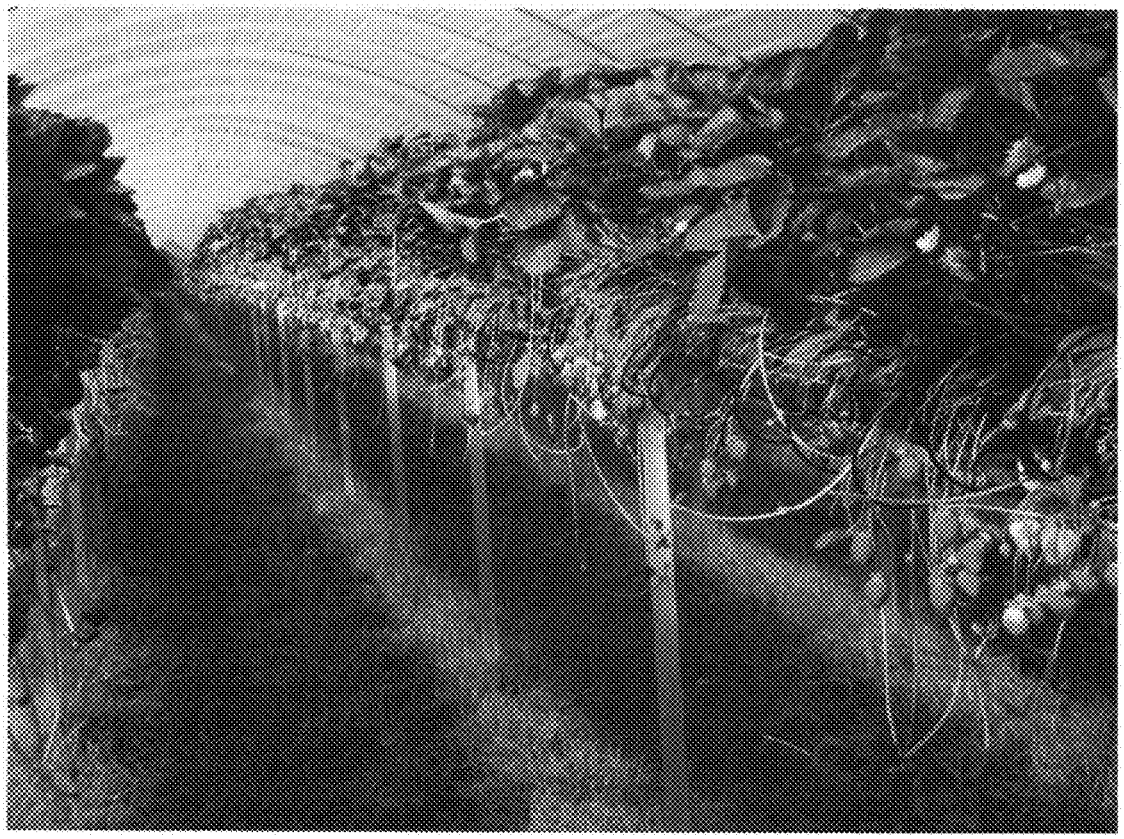
Figure 2:
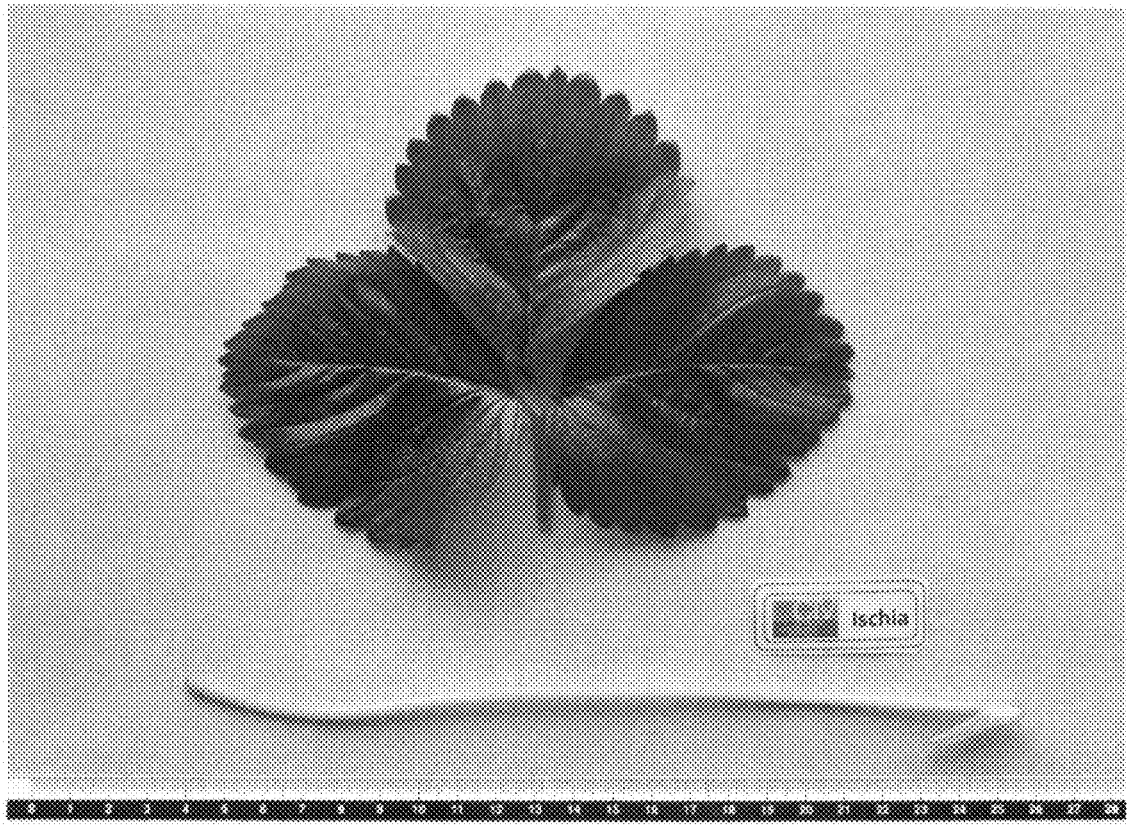
Figure 3:
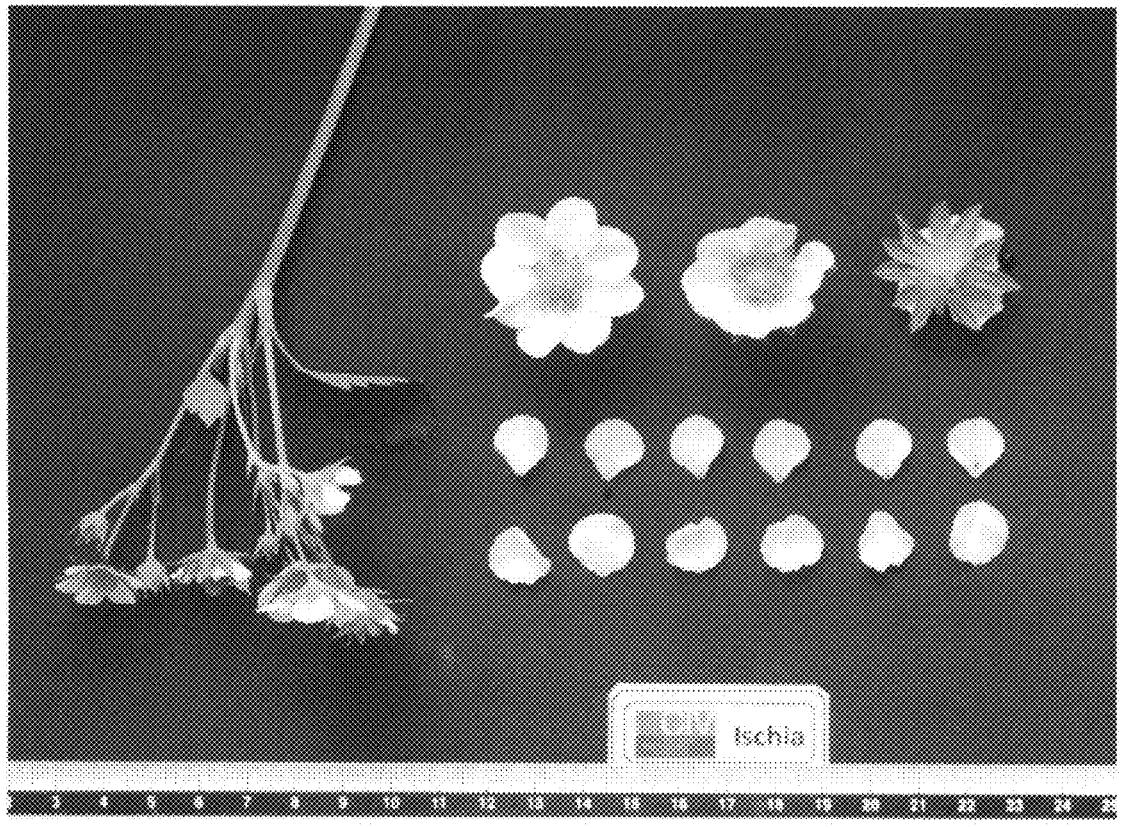
Figure 4:
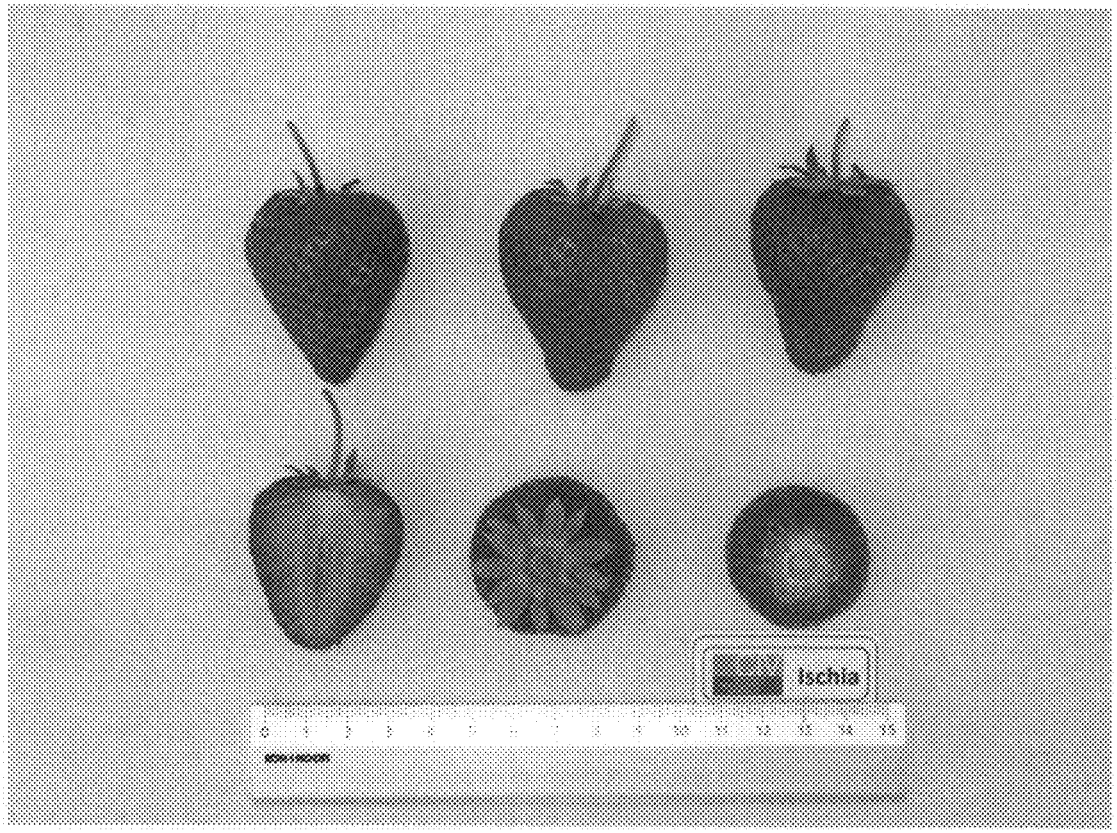

FIG. 1 shows the plant of 'ISCHIA';
FIG. 2 shows the leaves of 'ISCHIA';
FIG. 3 shows the flowers of 'ISCHIA'; and
FIG. 4 shows the fruits of 'ISCHIA'.

The colors of this illustration may vary with lighting conditions and, therefore, color characteristics of this new variety should be determined with reference to the observations described herein, rather than from these illustrations alone.

DETAILED BOTANICAL DESCRIPTION

The following detailed description of the 'ISCHIA' variety, unless otherwise noted, is based on observations taken of plants and fruits, and asexually reproduced progeny, grown at S. Giuseppe di Comacchio, Ferrara, Italy.

The observed plants were one year old plants. The plants used in the production field are produced in a nursery in S. Giuseppe di Comacchio, dug in December, cold stored, and planted in production fields in the middle of April.

Certain characteristics of this variety may change with changing environmental conditions (e.g., light, temperature, moisture, etc.), nutrient availability, or other factors. Quantified measurements are expressed as an average of measurements taken from a number of individual plants of the new variety. The measurements of any individual plant, or any group of plants, of the new variety may vary from the stated average. Color descriptions and other terminology are used in accordance with their ordinary dictionary descriptions, unless the context clearly indicates otherwise. Color designations are made with reference to The Royal Horticultural Society (R.H.S.) Color Chart.

Plant:

*Habit.*—Semi-upright.
*Density.*—Dense.
*Vigor.*—Medium.
*Overall shape.*—Semi-upright.
*Height.*—0.27-0.30 meters.
*Width.*—0.35-0.37 meters.

Leaf:

*Color of upper side.*—RHS 139A green group; color of under side: RHS 147B yellow green group.
*Size of leaf.*—Medium.
*Length.*—Average 12.9 cm.
*Width.*—Average 14.9 cm.
*Leaf surface ondulation or blistering.*—Medium.
*Leaf texture.*—Upper surface: medium/strong glossiness; medium blistering. Under surface: medium vein expression.
*Leaf arrangement.*—Slightly overlapping.
*Number of leaflets.*—Three only.
*Petiole.*—Length: About 19 cm. Diameter: 2.9 mm. Texture: hairy. Position of hairs: upwards. Density of hairs: Sparse. Color: RHS 145A yellow-green group.
*Stipule.*—Length: 29 mm. Width: 7.9 mm. Pubescence: Weak. Color: RHS 138B, green group. Anthocyanin coloration: Absent.
*Terminal leaflet.*—Length/width ratio: Moderately Longer. Length: About 7 to 8 cm. Width: About 6 to 7 cm. Shape of Terminal leaflet: Ovate. Shape of base: Obtuse. Shape of apex: Rounded. Margin: Serrate to Crenate. Texture: upper surface: medium/strong glossiness; medium blistering. under surface: medium vein expression. Shape in cross section: Concave.
*Stolons.*—Number about 5-6. Thickness: Medium, about 2.85 mm. Pubescence: Sparse. Color RHS 145A, yellow-green.

Inflorescence:

*Position relative to foliage.*—At same level or slightly below.
*Length.*—About 13-15 cm.
*Flower.*—Form: Rosaceae. Size: Medium. Arrangement of petals. Overlapping. Diameter of primary flowers. About 3.2 cm. Diameter of secondary flowers. About 2.5 cm. Flower depth (height of the corolla): 10 to 12 mm, measured when the flowers are fully open. Fragrance: No significant fragrance.
*Petals.*—Number of petals: 5 to 7. Shape: Circular, slightly elongated. Margin: entire. Apex: Rounded. Base: Obtuse/Nearly Right Angle. Texture (both surfaces): Smooth. Length: 13.2 mm. Width: 12.42 mm. Length/Width ratio: slightly elongated; 1.06. Color (Upper and Under Surface): RHS 155D, white group. Time from bloom to mature fruit: About 35 to 38 days.
*Calyx in primary flowers.*—Diameter: average 3.4 cm. Size of calyx relative to corolla: Same size or slightly larger.
*Sepal.*—Arrangement: Free. Shape: Elliptical. Apex: Convex. Margin: Entire. Length: about 10 mm. Width: about 4.0 mm. Number per flower: 12 to 16. Color of upper side: RHS 137B, green group. Color of under side: RHS 138B, green group. Texture (both surfaces): Hairy. Pubescence: weak.

Reproductive organs:

*Stamens.*—Numerous with pollen present, fertile and abundant. Length: approximately 3 mm. Color: near RHS 157A, green-white.
*Anthers.*—Generally average in size. Length: About 1.2 mm. Width: About 1 mm. Color: RHS 14 B yellow-orange; darkening with advanced maturity.
*Pollen.*—Fertile and abundant. Color: RHS 17 B yellow-orange.
*Pistils.*—Numerous, generally average in size. Color: RHS 151D yellow-green.

Fruit:

*Fruit truss.*—Attitude: Semi-erect.
*Ratio of length/maximum width.*—Moderately longer.
*Color of mature fruit.*—RHS 46A to 46B red.
*Color of flesh.*—RHS 34A orange-red, RHS 33B orange-red, and RHS 155D white.
*Length.*—40-50 mm.
*Width.*—37-45 mm.
*Calyx diameter.*—25-30 mm.
*Average weight.*—20-31 grams.
*Achene color.*—RHS 152C yellow green.
*Number of achenes per berry.*—480-520.
*Achene size.*—Length about 1.4 mm, width about 1 mm.
*Weight of* 1000 *achenes.*—0.40 grams.
*Peduncle length* (*of inflorescence stem*).—Primary fruit about 9-11 cm, secondary fruit about 6-7 cm.
*Peduncle diameter.*—1.9 mm.
*Peduncle color.*—RHS 139D green group.
*Peduncle texture.*—Hairy.
*Marketable yield* (*gm/plant*).—About 800-1000 grams.
*Fruit size.*—Large.
*Predominant shape.*—Conical.
*Difference in shapes between primary and secondary fruit.*—Slight.
*Band without achenes.*—Absent to very narrow.
*Unevenness of surface.*—Even or very slightly uneven.
*Evenness of color.*—Even or very slightly uneven.
*Glossiness.*—Medium.
*Insertion of achenes.*—Level with surface.
*Insertion of calyx.*—Inserted.
*Attitude of the calyx.*—Outwards.

*Size of calyx in relation to fruit diameter.*—Slightly smaller.

*Adherence of calyx.*—Medium.

*Firmness of flesh.*—Firm.

*Hollow center expression.*—Absent or small.

*Flavor.*—Good.

*Soluble solids* (% *brix*).—8.5-10.

*Time of first flowering.*—About 28-32 days after planting using cold stored plants quality A. Typically in S. Giuseppe di Comacchio Ferrara (Italy), planting beginning of April and first flowering beginning of May.

*Time of first harvesting.*—About 35-38 days after first flowering.

*Harvest period.*—June to November.

*Type of bearing.*—Fully remontant.

Disease resistance: The 'ISCHIA' variety has been tested for several years and it has not shown particular problems in cultivation. No specific testing for disease resistances has been carried out. In high humidity weather conditions 'ISCHIA' could be susceptible to *Phytophthora cactorum.* 'ISCHIA' has a good tolerance to powdery mildew.

What is claimed is:

1. A new and distinct variety of *Fragaria L.* plant named 'ISCHIA', as illustrated and described herein.

* * * * *